(12) United States Patent
Mirov (10) Patent No.: US 11,727,792 B2
(45) Date of Patent: Aug. 15, 2023

(54) OPTO-ELECTRONIC BIOPOTENTIAL CONTROLLER

(71) Applicant: NextSense, Inc., Mountain View, CA (US)

(72) Inventor: Russell Mirov, Los Altos, CA (US)

(73) Assignee: NextSense, Inc., Mountain View, CA (US)

( * ) Notice: Subject to any disclaimer, the term of this patent is extended or adjusted under 35 U.S.C. 154(b) by 728 days.

(21) Appl. No.: 16/682,621

(22) Filed: Nov. 13, 2019

(65) Prior Publication Data

US 2021/0142657 A1 May 13, 2021

(51) Int. Cl.
*G08C 23/06* (2006.01)
*A61B 5/296* (2021.01)
*A61B 5/245* (2021.01)
*A61B 5/25* (2021.01)
*G06F 3/01* (2006.01)

(52) U.S. Cl.
CPC .............. *G08C 23/06* (2013.01); *A61B 5/245* (2021.01); *A61B 5/25* (2021.01); *A61B 5/296* (2021.01); *G06F 3/015* (2013.01); *A61B 2560/0223* (2013.01)

(58) Field of Classification Search
CPC ........... G08C 23/06; A61B 5/245; A61B 5/25; A61B 5/296; A61B 2560/0223; A61B 5/30; A61B 5/1495; A61B 2560/0233; G06F 3/015
See application file for complete search history.

(56) References Cited

U.S. PATENT DOCUMENTS

| | | |
|---|---|---|
| 6,871,084 B1 | 3/2005 | Kingsley et al. |
| 7,447,534 B1 | 11/2008 | Kingsley et al. |
| 8,838,218 B2 | 9/2014 | Khair |
| 2002/0161309 A1 | 10/2002 | Marro |

(Continued)

OTHER PUBLICATIONS

International Search Report and Written Opinion for Application No. PCT/US2020/032646 dated May 20, 2021.*

(Continued)

*Primary Examiner* — Mark W. Bockelman
(74) *Attorney, Agent, or Firm* — Perkins Coie LLP (57) ABSTRACT

The technology provides a system and method for simulating and detecting bio signals such as brain bio-signals. Optical fibers provide modulated signals received from an optical signal modulator. The modulated signals are received by a set of emission elements disposed within the phantom body, which output corresponding electrical signals. The electrical signals are detected by a set of sensors and evaluated by a receiver device, such as for an electroencephalograph (EEG), electrocardiogram (ECG), electromyogram (EMG) or magnetoencephalography (MEG) diagnostic system. A controller manages the modulation of light signals so that specific electrical signals can be generated as desired. Because tens, hundreds or thousands of emission elements may be arranged in the phantom body, the controller can manage operation of the optical signal modulator so that the precise physical location of each emission element can be mapped quickly and efficiently. The controller may also detect defective components in a similar manner.

20 Claims, 9 Drawing Sheets

(56) References Cited

U.S. PATENT DOCUMENTS

| | | |
|---|---|---|
| 2005/0145786 A1 | 7/2005 | Rice et al. |
| 2006/0199159 A1 | 9/2006 | Ghiron et al. |
| 2012/0275178 A1 | 11/2012 | Logunov |
| 2017/0281014 A1 | 10/2017 | Von Luehmann et al. |
| 2018/0033339 A1 | 2/2018 | Kerins et al. |
| 2021/0137400 A1 | 5/2021 | Mirov |

OTHER PUBLICATIONS

Safaie, J., et al., "Toward a fully integrated wireless wearable EEG-NIRS bimodal acquision system", IOP Science, May 2019, pp. 1-3.

Schwerdt, Helen N., et al., "A Fully Passive Wireless Backscattering Neurorecording Microsystem Embedded in Dispersive Human-Head Phantom Medium", IEEE Electron Device Letters, vol. 33, No. 6, Jun. 2012, pp. 908-910.

Schwerdt, Helen N., "Fully Passive Wireless Acquisition of Neuropotentials", Arizona State University, Aug. 2014.

Schwerdt, Helen N., et al., "Wireless Fully Passive Multichannel Recording of Neuropotentials Using Photo-Activated RF Backscattering Methods", IEEE Transactions on Microwave Theory and Techniques, vol. 63, No. 9, Sep. 2015, pp. 2965-2970.

Symeonidou, Evangelia-Regkina, "Effects of Cable Sway, Electrode Surface Area, and Electrode Mass on Electroencephalography Signal Quality during Motion", Sensors, 2018, 18, 1073, pp. 1-13.

Tsizin, E., et al., "Printable anisotropic phantom for EEG with distributed current sources", Aug. 19, 2018, pp. 1-18.

Von Luhmann, Alexander, et al., "M3BA:A Mobile, Modular, Multimodal Biosignal Acquisition Architecture for Miniaturized EEG-NIRS-Based Hybrid BCI and Monitoring", EMB IEEE Transactions on Biomedical Engineering, vol. 64, No. 6, Jun. 2017, pp. 1199-1210.

International Search Report and Written Opinion for Application No. PCT/US2020/032635 dated Jul. 28, 2020.

Imai, Daigo, et al., "Realistic dynamic brain phantom and time-resolved measurement", SPIE—International Society for Optical Engineering. Proceedings, vol. 3597, Jul. 15, 1999., pp. 1-12.

USPTO, Non-Final Office Action for U.S. Appl. No. 16/682,570, dated Jan. 20, 2023, 18 pages.

* cited by examiner

OPTO-ELECTRONIC BIOPOTENTIAL CONTROLLER

CROSS-REFERENCE TO RELATED APPLICATION

The present application is related to U.S. application Ser. No. 16/682,570, entitled Optically Excited Biopotential Phantom, Attorney Docket No. ATOZX 3.0E-2052 II [9039], filed concurrently herewith, the entire disclosure of which is incorporated by reference herein.

BACKGROUND

Physical bio-phantoms have been used to simulate various types of human tissue, including the brain. In this type of system, a set of electrodes may be placed at various points along the phantom by running wires through it. The electrodes are actuated with electrical pulses. However, the placement and amount of wiring may create interference (e.g., crosstalk) that can adversely impact signal quality and prevent accurate signal evaluation. For instance, magnetoencephalography (MEG) may be significantly affected by electrical crosstalk.

BRIEF SUMMARY

The technology relates to a system for simulating bio signals such as brain bio-signals, as well as detection and evaluation of such signals. This system can be used for medical or non-medical purposes, e.g., to simulate or evaluate certain medical conditions, to provide a brain control interface (BCI) for a computer application, etc. As discussed further herein, a physical brain-type phantom is employed that is configured to simulate various biopotentials in a repeatable and calibrated manner. Furthermore, the phantom structure does not need to be homogenous. Rather, it may have different layers or regions to mimic the skull, brain, skin, hair, etc.

According to one aspect, optical fibers are arranged within the phantom to convey a modulated light signal to a particular location in or along the phantom. The end of each fiber is coupled to a photoreceiver. Each photoreceiver can be operated in a photovoltaic mode to produce a photoelectric effect, with the resulting electrical signals capable of being detected by, e.g., an electroencephalograph (EEG), electrocardiogram (ECG), electromyogram (EMG) or MEG sensor. A controller is employed to manage the modulated light signals along each fiber so that specific electrical signals can be generated at each particular photoreceiver as desired, for instance to emulate particular brain functionality.

A biopotential control system is provided for use with a biological phantom to simulate one or more biopotentials. In this aspect of the technology, the system comprises an optical control module having one or more optical signal generators, one or more optical signal modulators, and a controller. The one or more optical signal generators are configured to emit light to excite a plurality of optodes disposed within the biological phantom. The one or more optical signal generators are coupled to a plurality of optical fibers each having a portion thereof received within a body structure of the biological phantom. And each optical fiber is operatively coupled to a corresponding one of the plurality of optodes. The one or more optical signal modulators are coupled to the one or more optical signal generators. The one or more optical signal modulators are configured to vary at least one of an intensity, pulse width, pulse repetition rate, polarization, or color of the light emitted by the one or more optical signal generators. And the controller is coupled to one or both of the optical signal generators and the optical signal modulators. The controller is configured to vary one or more parameters of the optical signal generators or the optical signal modulators to cause selected ones of the plurality of optodes within the biological phantom to generate electrical signals in order to simulate the one or more biopotentials.

In one example, the biopotential control system further comprises a receiver module including a set of sensors configured to detect electrical signals generated by the plurality of optodes in response to a simulated biopotential. Here, the set of sensors of the receiver module may be selected from the group consisting of electroencephalograph (EEG), electrocardiogram (ECG), electromyogram (EMG) or magnetoencephalography (MEG) sensors. The controller may also be configured to receive feedback from the receiver module to map physical locations of the optodes within the body structure of the biological phantom. The one or more optical signal generators may be lasers or light emitting diodes (LEDs). The one or more optical signal generators can be arranged as a one-, two-, or three-dimensional LED matrix.

The one or more optical signal generators may comprise a plurality of optical signal generators, in which each of the plurality of optical signal generators is optically coupled to a given one of the plurality of optical fibers. The one or more optical signal modulators may comprise a one or two-dimensional array of light shutters.

In one example, the biopotential control system further comprises the plurality of optical fibers. Alternatively or additionally, the biopotential control system further comprises the biological phantom and the plurality of optodes.

The controller may be further configured to calibrate the biopotential control system to account for channel-by-channel variability due to at least one of manufacturing tolerances, aging, electrochemical shifts in the body structure of the biological phantom, or environmental conditions. The controller can also or additionally be further configured to identify a defect in one of the plurality of optical fiber, one of the plurality of optodes, a modulation path, a sensor or a receiver module.

According to another aspect of the technology, a method of simulating one or more biopotentials for a biological phantom is provided. The method comprises emitting, by one or more optical signal generators, light to excite a plurality of optodes disposed within the biological phantom; varying, by one or more optical signal modulators, at least one of an intensity, pulse width, pulse repetition rate, polarization, or color of the light emitted by the one or more optical signal generators to generate a selected light pattern; and varying one or more parameters of the optical signal generators or the optical signal modulators to cause selected ones of the plurality of optodes within the biological phantom to generate electrical signals in response to the selected light pattern in order to simulate the one or more biopotentials.

The one or more biopotentials may correspond to one or more types of brain activity. For instance, the one or more types of brain activity may be selected from the group consisting of Alpha waves, Beta waves, Delta waves, Theta waves, sleep spindles, slow-waves and seizure activity.

The method may further comprise repeating the varying of the one or more parameters to cause the plurality of optodes to reproduce the generated electrical signals one or more times. Alternatively or additionally, the method also includes multiplexing the selected light pattern across a set of optical fibers, where each of the optical fibers in the set is coupled to a corresponding one of the plurality of optodes. The method may also include calibrating an optical modulation and control module in response to the simulated one or more biopotentials. And varying the one or more parameters of the optical signal generators or the optical signal modulators can be performed based on a 2D or 3D arrangement of the plurality of optodes within the biological phantom.

And in accordance with another aspect of the technology, the method comprises providing a biological phantom having a set of optodes disposed therein, the set of optodes configured to operate in a photoresponsive mode, each one of the set of optodes being optically coupled to a corresponding one of a set of optical fibers; coupling the set of optical fibers to one or more light sources; actuating, by a controller, the one or more light sources to generate at least one test signal that is propagated along the set of optical fibers; detecting, by a set of sensors, electrical signals emitted by the set of optodes in response to the propagated at least one test signal; and mapping, by the controller, a location of each optode within the biological phantom.

The at least one test signal can include distinct signals applied to one or more of the optical fibers. Actuating the one or more light sources to generate the at least one test signal may be performed to propagate the at least one test signal along one fiber at a time. Actuating the one or more light sources to generate the at least one test signal may be performed using time division multiplexing. Actuating the one or more light sources to generate the at least one test signal may include the controller actuating an array of light shutters to produce time varying pixels associated with individual fibers of the set of optical fibers. Actuating the one or more light sources to generate the at least one test signal can include varying one or more of an intensity, pulse width, pulse duration, polarization or color of the at least one test signal.

Mapping the location of each optode within the biological phantom may include evaluating the detected electrical signals based on known locations of the set of sensors. Here, evaluating the detected electrical signals based on known locations of the set of sensors may include performing triangulation or trilateration to identify a specific location of a given optode of the set of optodes within the biological phantom.

Actuating the one or more light sources to generate the at least one test signal can comprise modulating optical signals so that the electrical signals emitted by the set of optodes have amplitudes that exceed a threshold value.

The method may further comprise performing a calibration operation based on the mapping of the location of each optode within the biological phantom. The calibration operation can include identifying one or more of a defective optical fiber, a defective optode, or a defective sensor. The calibration operation can alternatively or additionally include performing a normalization process to account for variations in signal level of the electrical signals emitted by the set of optodes.

The method may further comprise detecting either (i) failure of a given optode in the set of optodes or (ii) failure to propagate the at least one test signal along a given fiber of the set of optical fibers. In response to the detecting of (i) or (ii), the controller adjusts either a modulation technique or the one or more light sources. And adjusting either the modulation technique or the one or more light sources can include modifying the at least one test signal propagated along the set of optical fibers to produce a selected pattern by the optodes that have not failed.

DETAILED DESCRIPTION

Figure 1:
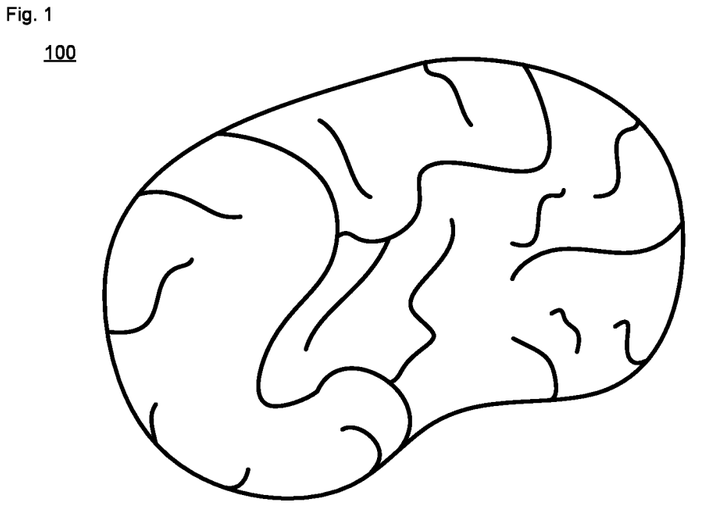
FIG. 1 illustrates an example brain to emulate in accordance with aspects of the technology.

FIG. 1 illustrates one type of biological tissue 100, in particular a brain, that can be emulated according to the technology disclosed herein. The human brain is a soft tissue structure that includes billions of neurons and many more synaptic connections disposed throughout a complex 3D framework. As noted above, a bio-phantom can be used to simulate certain brain activity. However, arranging the wiring and placement of electrodes in a bio-phantom may be challenging, even for a small amount of electrodes. Furthermore, crosstalk or other interference can corrupt signals, rendering them unsuitable for medical or non-medical purposes (e.g., diagnostics, BCI). The following provides a bio-phantom architecture and emulation system that minimizes such problems and enables robust testing and analysis. For instance, bio-phantoms as discussed herein can be used to create electrical signals that are detectable by various types of sensors used for symptom evaluation, analytics or other purposes.

Example Implementation

Figure 2A:
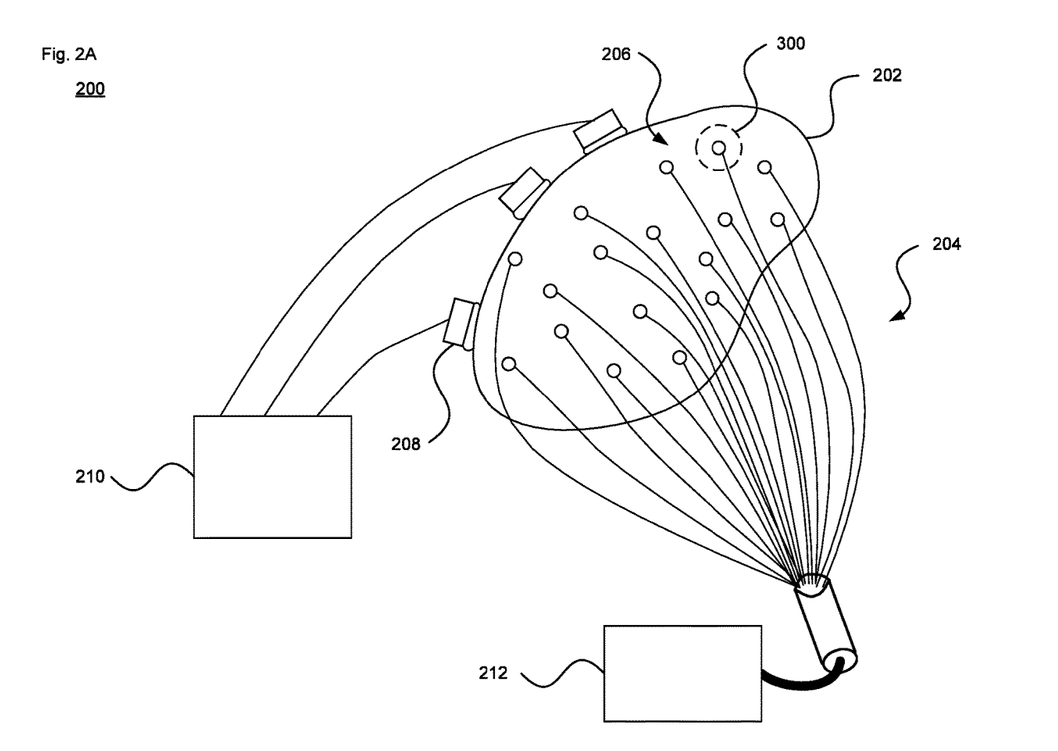
FIGS. 2A-B illustrate an example bio-phantom system in accordance with aspects of the technology.

FIG. 2A illustrates an example bio-phantom system 200 including a phantom body structure 202, a set of optical fibers 204, and a corresponding set of emission elements such as photoreceivers or other optical electrodes ("optodes") 206 disposed within or otherwise about the phantom body structure 202. The system 200 also includes a set of sensors 208, which are coupled to a receiver device 210, as well as an optical modulation and control module 212 that is coupled to the set of optical fibers 204.

Figure 2B:
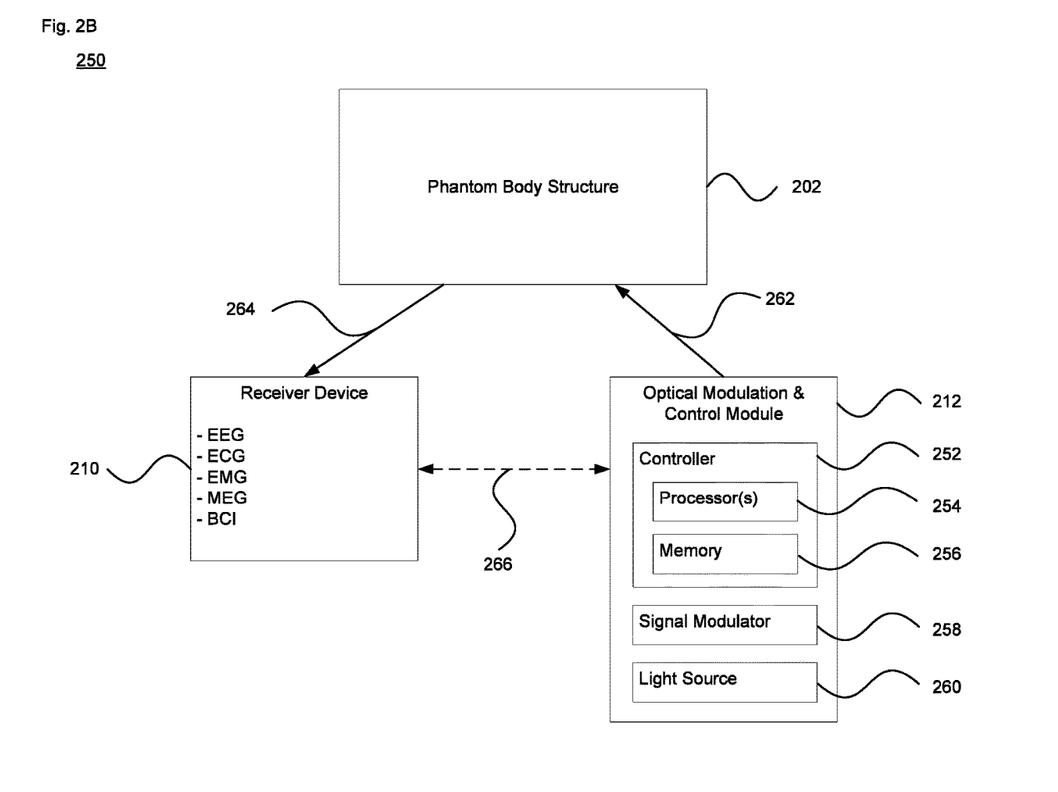

FIG. 2B illustrates a functional view 250 of the example bio-phantom system of FIG. 2A. The receiver device 210 may be a diagnostic or computing system. By way of example, diagnostic systems such as EEG, ECG, EMG or MEG systems can be employed. Alternatively, the receiver device 210 may be part of or coupled to a BCI system.

Effective use of the bio-phantom system 200 can include modulating the light signals passed through some or all of the optical fibers 204, in order to mimic specific biological patterns, either normal or atypical. As discussed further below, in addition to managing the light modulation for each fiber, the optical modulation and control module 212 is also able to provide system diagnostic checks, facilitate calibration adjustments, and provide an interface to load and run arbitrary user specified simulations. It may receive feedback from the receiver device (EEG, ECG, EMG, MEG, etc.) in conjunction with such operation.

As shown, the optical modulation and control module 212 includes a controller 252 having one or more processors 254 and memory 256, as well as an optical signal modulator 258. Memory 256 stores instructions and data that may be executed or otherwise used by the processor(s) 254. The one or more processors 254 may be, e.g., a controller or CPU. Alternatively, the one or more processors 254 may be a dedicated device such as an ASIC, DSP, FPGA or other hardware-based device. The memory 256 may be of any type capable of storing information accessible by the processor(s) in a non-transitory manner, such as solid state flash memory, hard disc, optical medium or the like.

The instructions may be any set of instructions to be executed directly (such as machine code) or indirectly (such as scripts) by the processor(s). For example, the instructions may be stored as computing device code in the non-transitory memory. In that regard, the terms "instructions" and "programs" may be used interchangeably herein. The instructions may be stored in object code format for direct processing by the processor(s), or in any other computing device language including scripts or collections of independent source code modules that are interpreted on demand or compiled in advance. The data may be retrieved, stored or modified by one or more processors in accordance with the instructions. As an example, the data may comprise one or more modulation schemes to be used in a training system, where the modulation schemes are associated with one or more brainwave patterns, medical conditions or stimuli to be evaluated by the training system.

The signal modulator 258 is configured to set or modulate one or more light patterns that are to be propagated along the set of optical fibers from one or more light sources 260. The light source(s) 260 may be incorporated into the module 212 or be a separate source. By way of example, the light source 260 may comprise one or more LEDs arranged in a linear array or 2D matrix. This optical modulation approach can provide effectively arbitrarily high bandwidth, which can permit finely tuned waveform patterns. Here, light output from the light source 260 may be time multiplexed across some or all of the fibers in the set.

The light patterns can be applied to one, some or all of the optical fibers in the set. As shown by arrow 262, the light patterns are received by the phantom body structure 202. As described in more detail below, the optodes generate electrical signals in response to the received light patterns, and those electrical signals are detected by the sensors. As shown by arrow 264, the detected signals are passed to the receiver device 210 for processing. And as indicated by dashed arrow 266, the optical modulation and control module 212 and the receiver device 210 may be in direct or indirect communication with one another. This may be done, for instance, to provide feedback to the module 212 as part of a machine learning or other training operation.

The signal modulator 258 is able to generate repeatable optical signals in response to instructions from the controller 252. Such optical signals can include one or more patterns for emulating selected types of brain activity. In particular, modulation of the light source(s) will result in different waveform patterns. The controller 252 may be programmed with waveform patterns to simulate normal and pathological conditions. As a result, the optical signals generated by the signal modulator and propagated through the set of optical fibers will cause the optodes to emit electrical signals in different patterns corresponding to the selected brain activity. By way of example, the brain activity may include, e.g., Alpha, Delta, Theta, and Beta waves. "Sleep Spindles", slow-waves, and different types of seizures.

This arrangement allows for a repeatable approach that can be used for testing of different conditions and scenarios. It also enables calibration of the sensors and the receiver device. In particular, because the optical approach avoids crosstalk or other interference, the system can repeatedly produce the same waveform patterns with high fidelity. This allows one to develop and calibrate equipment that is particularly beneficial in research and clinical settings. In another approach, machine learning techniques can be employed with the system, for instance to help identify particular medical conditions, or to associate particular brain activity with instructions used to control a computing device or other component as part of a BCI system.

Example Implementation and Operation

According to one aspect of the technology, the set of optical fibers 204 is at least partly arranged within the phantom body structure 202. A first end of each optical fiber is coupled to the optical modulation and control module 212, while an opposing second end is disposed within the phantom body structure 202 remote from the module 212. Each fiber is configured to convey a modulated light signal to a particular location along or otherwise within the phantom body structure. The modulation can be accomplished in various ways by the optical modulation and control module. This can include varying the intensity (amplitude), pulse width, pulse duration, polarization and/or color, etc. of the propagated light. While feasible, there is no need to include data, embedded a clock signal or provide other information to the phantom body structure. Instead, the goal with this approach is to vary the intensity illumination so that the resulting voltage generated by a given optode reflects the desired waveform.

In particular, modulated pulses may be sent rapidly or slowly to mimic corresponding biological signals, such as the firing of neurons. For instance, neural spiking rates can be significantly lower than even 100 times a second, for example down at 1-20 spikes/second. The rate may be low, but the precision that the system can deliver that relatively infrequent spike might be important for the biological signal of interest. Thus, activation of a given optode (or set of optodes) may need to occur with milli- or micro-second precision. Furthermore, even if the control system is remotely located from the phantom, for instance tens or hundreds of feet from an EMI-shielded room containing the phantom, any loss in optical signal strength or quality is effectively de minimis.

Figure 3:
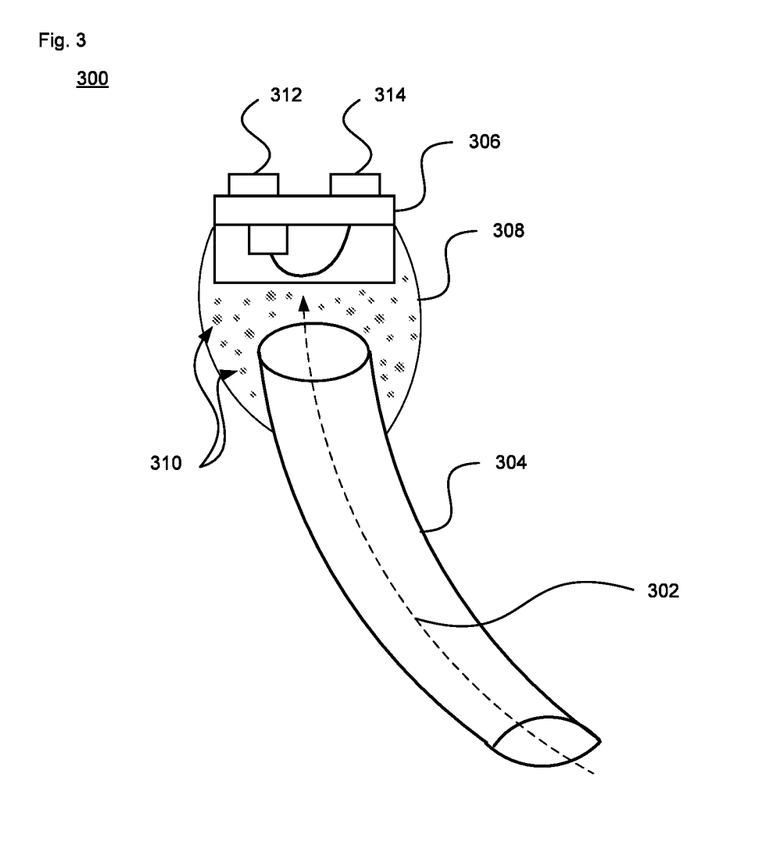
FIG. 3 illustrates an example optical fiber-photoreceiver coupling in accordance with aspects of the technology.

As shown in FIG. 2A, the second end of each fiber is coupled to a respective optode. Each optode may be, e.g., a photodiode or light-emitting diode (LED) such as a surface mount LED. FIG. 3 illustrates an enlarged view of dashed region 300 of FIG. 2A. As shown in this view by dashed line 302, a modulated optical signal is propagated along optical fiber 304 towards optode 306. While in one example the optode 306 may be directly connected to the optical fiber 304, in another example optical coupling may be accomplished using an optically clear adhesive 308 or other coupling mechanism.

Significant advantages to this approach are that little to no detectable signal loss occurs along the fiber, and there is effectively no crosstalk between the fibers, either leading into the phantom body structure or within the phantom body structure itself. Avoidance of such signal degradation or interference makes the system operation repeatable and robust. One benefit of this is the ability to use fibers of any needed length, which is particularly helpful when the phantom body structure is located in a shielded enclosure (e.g., for MEG testing) and the optical modulator and/or overall control system is located remote from or otherwise outside of the shielded enclosure. For instance, each fiber may be, e.g., 1 m, 10 m, 100 m in length, or more or less. The optical fibers may be single mode or multi-mode.

In one scenario using an optically clear adhesive, the adhesive may be applied and cured using a UV light source. Here, a phosphor slurry or other additive, as shown by speckled elements 310, the may be incorporated with the adhesive to extend (stretch) the time each light pulse is incident on the optode. This may be done to avoid a flicker effect at the optode. According to one aspect, the phosphor slurry or other additive may be particularly beneficial in instances where the optical modulation involves one or more sets of brief light pulses across a series of fibers. By way of example, rapid pulsing of the light source for one or more fibers would result in rapid electrical pulses appearing at the corresponding optode in the phantom body structure.

Figure 4A:
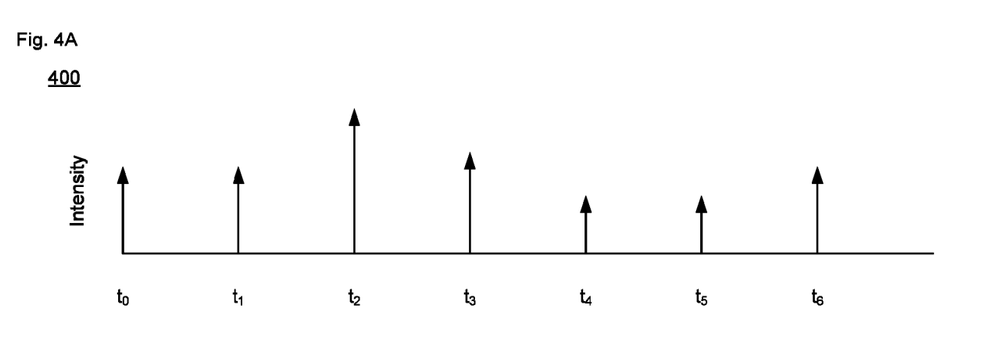
FIGS. 4A-B illustrate light pulse responses in accordance with aspects of the technology.
Figure 4B:
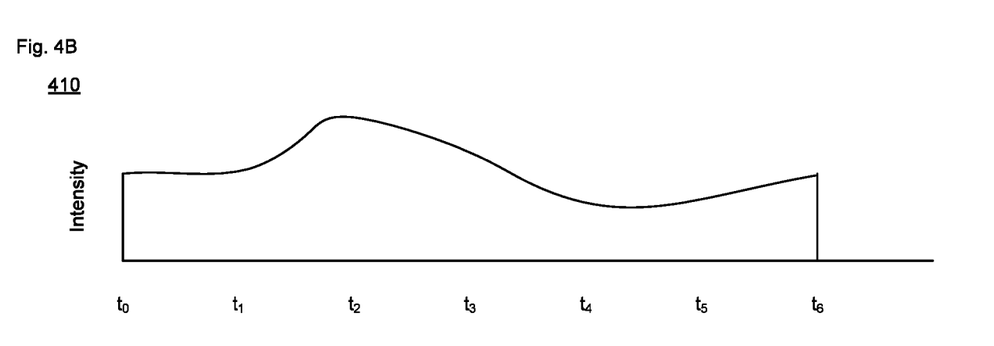

Use of a phosphor slurry could modify this to result in a continuous fading trail ("glow") rather than discrete pulses. FIGS. 4A-B illustrate an example of a fading trail in response to a series of light pulses. In particular, FIG. 4A illustrates a view 400 of a series of light pulses of different intensities at times $t_0, t_1, \ldots t_6$, which may be generated by the signal modulator as directed by the controller. By way of example, each pulse may last less than 10 ms, for instance 0.1-5.0 ms, or more or less. The time between pulses may be on the order of 10-50 ms, or more or less, and the time between pulses may vary.

In this example, while the view 400 shows the pulses as occurring with uniform spacing in time, this need not be the case. Rather, adjacent pulses may occur more quickly or slowly depending on the type(s) of signals the system is emulating, and the type(s) of resultant electrical patterns desired. By way of example only, the time between $t_0$ and $t_1$ may be 10 ms, while the time between $t_1$ and $t_2$ may be 20 ms. The intensity may vary on an absolute or relative scale, for instance, from 1% to 100% of maximum intensity. FIG. 4B illustrates another view 410, in which the slurry provides a persistent, fading light instead of instantaneous pulses, thereby prolonging the time the light is visible to the sensors. Thus, in this scenario, one or more fibers can receive a very narrow pulse of high intensity, where the phosphor is able to stretch out the pulse to remove flicker.

The choice of source light wavelength may be based on the sensitivity of the detector(s) and the availability of the source. The phosphor type and slurry composition may also be varied. For instance, a particular arrangement may be selected to absorb energy at a particular wavelength and re-emit at another (fluoresce). According to one scenario, if the goal is to emulate neural spiking in a human brain, then either no or a short-lifetime phosphor can be used. If slower frequency waveforms are desired, then a slower or longer lifetime phosphor can be employed as a low-pass filter or optical signal integrator.

The optodes can be operated in a photovoltaic mode to produce a photoelectric effect. For instance, the anode and cathode pads 312, 314 of each optode may be left exposed as shown in FIG. 3. These pads may be gold plated, and are thus relatively inert and highly conductive. As photons are emitted from the fiber and are received at the semiconductor junction of the optode, a potential (e.g., up to 1.5 volts or more or less) is developed across the anode/cathode junction. This, in turn, creates an electrical signal that is detectable, for instance, by an EEG, ECG, EMG, MEG or BCI sensor. The potential's amplitude is related to the intensity of the emitted light, in accordance with the modulation of the light. Thus, the controller may finely tune the electrical signals to be detected by the sensors by manipulating the emitted light intensity from the signal modulator.

A radiating element may act as a mechanism for getting more surface area of the optode in contact with the conductive substrate material of the phantom body structure. This may be of particular interest in situations where there is a low-density optode arrangement within the structure so that each optode needs to handle a larger area or volume. In very high density situations it may be more desirable for each fiber/detector endpoint to be as small as possible, so that the sensors are not receiving electrical signals from too many neighboring optodes.

The bulk material (body) of the phantom body structure should be selected to be weakly conductive so that that bulk material is able to effectively convey the electrical potentials generated by the optodes to the exterior surface of the phantom. For instance, salt ions or other charged particles may be incorporated within the bulk material to improve conductivity. The bulk material can be a liquid, gel, or even a solid. In one example, a ballistic gel or silicon rubber material may be employed. In another example, cells of a desired type may be mixed in agar to form the bulk material. And in a further example, the bulk material may be selected to be both weakly conductive and include particles capable of exhibiting the photo-voltaic effect. For instance, this may include a material in which very small silicon spheres or other nodules are patterned with electrodes, which can eliminate the need for discrete optodes coupled to the ends of the fibers. Here, phosphor could also be incorporated directly into the bulk material. The amount of conductivity throughout the structure, or in one or more localized regions within the structure, can be selected to mimic the tissue(s) under evaluation. By way of example, the brain, skull and scalp may all have different conductivities, and different bulk materials can be arranged to simulate such tissues. Furthermore, depending on the type of test and the particular use case, the phantom body structure may be shaped like the actual biological tissue(s), e.g., head, chest, etc., or it may have a general rectilinear, spherical or other shape.

In one scenario, a brain phantom configured as discussed above may include tens, hundreds or potentially thousands of optodes coupled to corresponding fibers. Each fiber may be less than 1 millimeter in diameter (e.g., 0.1-0.8 mm or more or less), and the spacing between the anode and cathode pads of the optode may be a fraction of a millimeter (e.g., 0.1-0.5 mm, or more or less). In addition, the fibers may include an outer cladding, or may not include any protective outer layer, which allows for them to have diameters smaller than 1 mm. The small size of the fibers and the photoreceiver structures thus enables the use of as many fiber/photoreceiver elements as desired.

Depending upon the electrical signals sought to be emulated, the optodes can be arranged in different 3D patterns within the phantom. The particular arrangement may vary depending on the biological counterpart and the type(s) of test to be conducted. For instance, the optodes may be sparsely arranged in one or more regions of the phantom while other regions are more densely populated. This can be done to simulate localized regions of activity, such as particular parts of the brain. By way of example only the frontal and temporal lobe regions of the phantom may be densely populated while the parietal and occipital lobe regions may be sparely populated. Thus, in one example the densely populated regions may have hundreds or thousands of optodes in total while the sparely populated regions may have 5-20 optodes in total, or more or less. In another example, the densely populated regions may have at least 10-50 optodes/cm$^3$, while the sparsely populated regions may have on the order of 1-5 optodes/cm$^3$, or more or less. In one scenario, the upper bound on the density of optodes is the neural density of the brain itself. In another scenario, the density of optodes may be limited by the physical size of each optode and/or the space available within the phantom body structure for the optical fibers.

The optodes may be held in place by some infrastructure (scaffolding) so that their physical positions relative to the outer sensing surface of the phantom can be maintained. By way of example, a scaffold may be constructed by, e.g., 3D printing. Once constructed, the optodes are attached. Fibers are routed along the scaffolding and optically coupled to the optodes. After the fibers are arranged as desired, phantom bulk material can be poured into the structure, where it may be maintained as a liquid or cured until it forms into a gel or a solid.

Figure 5A:
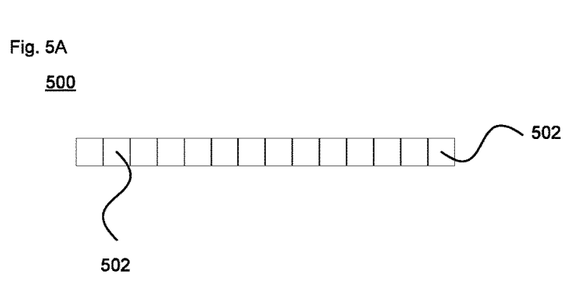
FIGS. 5A-B illustrates example light arrays in accordance with aspects of the technology.
Figure 5B:
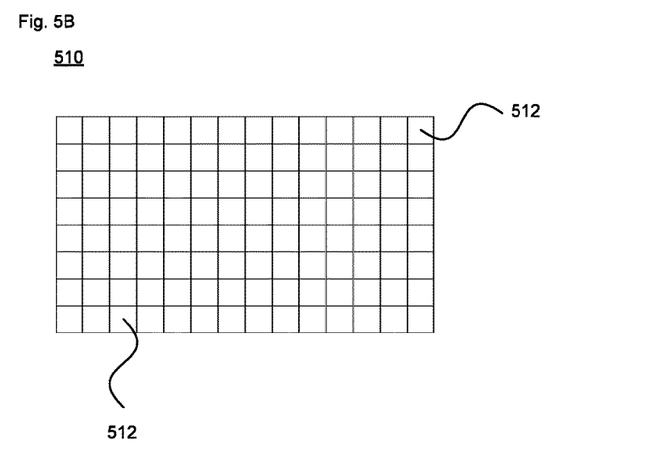

While configuring the optode and fiber placement in the phantom can be challenging, handling light distribution and modulation by the optical modulation and control module can be equally challenging, as it can include varying the intensity, pulse width or duration, polarization, etc. of the propagated light for each fiber. In a simple system with only a few fibers (e.g., 10 or fewer), one could have individual LEDs or lasers coupled to each respective fiber. Here, each light source can be modulated at the baseband information rate of the bio potential to be simulated using a local control circuit. In another example, an LED matrix can be pulse width modulated (PWM) via an embedded microcontroller that is part of the LED assembly, including varying the intensity and/or color. FIG. 5A illustrates one example 500 with a plurality of individual LED elements 502 arranged in a linear array. And FIG. 5B illustrates another example 510 with LED elements 512 arranged in a two-dimensional array.

Such approaches may be used to potentially control hundreds of fibers simultaneously. Nonetheless, the system is not limited to one- or two-dimensional LED arrays. According to one aspect, the light sources may be organized an a three-dimensional (e.g., cubic) array, or multiple planes of two-dimensional arrays.

Low-density solutions may not scale effectively when the number of fibers increases by an order of magnitude or more. For more complex arrangements, other approaches may be employed. In one scenario, the optical signal source may utilize time division multiplexing so that emitted light is provided to each individual fiber sequentially. This could be accomplished mechanically, electrically or optically. By way of example, a mechanical scanner might utilize a rotating mirror to scan a single modulated light source across the arc of the faces of an array of fibers such that as the deflected laser arrives at each fiber a selected modulation is timed to be delivered to that fiber.

In another scenario, the optical modulation module may use a one or two dimensional arrays of light shutters (or similar technology such as DLP, OLED, or vertical cavity surface emitting laser (VCSEL) arrays) to produce time varying pixels that can be associated (physically/optically) with individual fibers. This permits each fiber to receive a continuous light source with baseband modulation and without multiplexing. A very large number of fibers can be supplied signals with this approach (e.g., thousands or more).

Any of these approaches can provide modulation rates more than sufficient for biopotential simulation. These approaches can be all-digital, which permits very fine computer control of the system.

As noted above, when the phantom is fabricated, each optode may be placed at a specific 3D location within the phantom, and each corresponding fiber may be arranged within the body. This may be accomplished more easily when there are only a few fiber/photoreceiver sets to place, or when a scaffolding structure is employed. This way, prior to use the exact 3D location of each fiber/optode set may be known.

However, when many fiber/optode sets are incorporated into a phantom body structure, it may not be easy to place a given set at a particular location, especially when some fibers may be of different length, the phantom is formed using a liquid or gel-based bulk material, etc. This could potentially be problematic, because the control system needs to know which fiber/photoreceiver sets to excite at a particular time in order to implement a given biopotential simulation.

Figure 6:
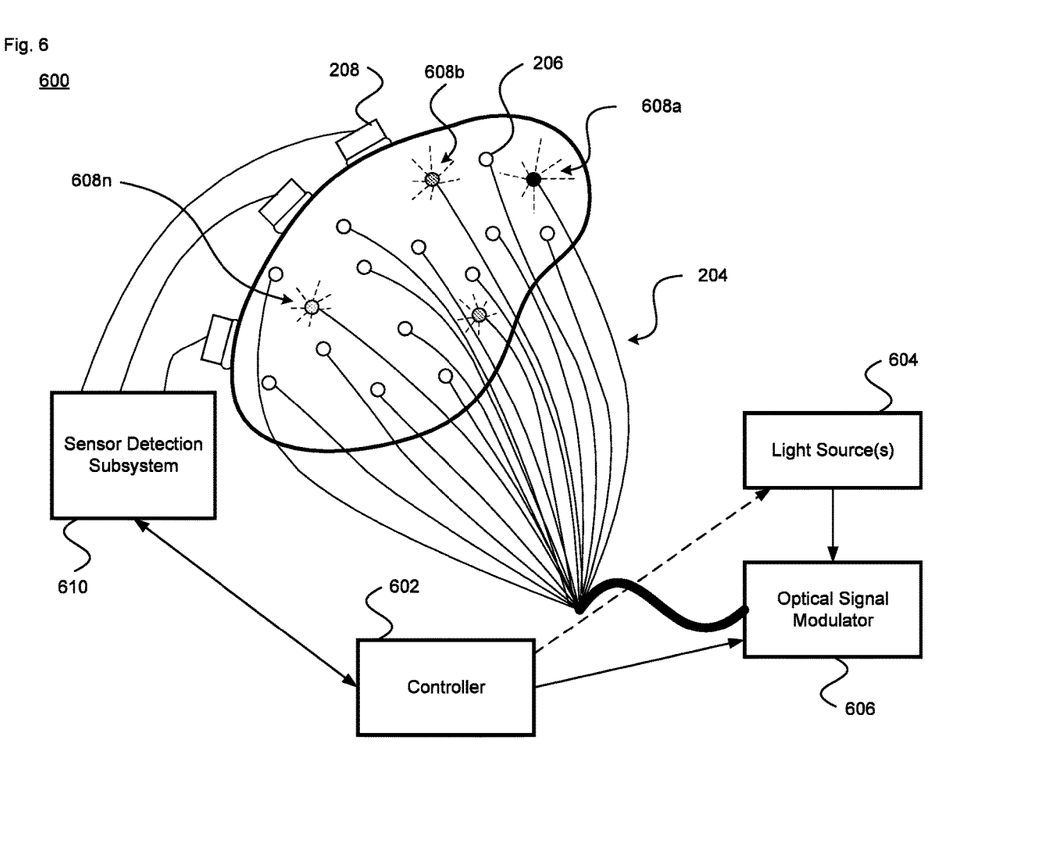
FIG. 6 illustrates a mapping technique in accordance with aspects of the technology.

Thus, according to one aspect of the technology, it may be much more efficient to install the fiber/optodes sets first and then map their locations after phantom fabrication. This can be done via feedback from a sensor detection subsystem, which can be, e.g., commercial sensing equipment (ECG, EEG, etc.). Scenario 600 of FIG. 6 illustrates a one such functional approach. Here, the ends of optical fibers 204 and optodes 206 of FIG. 2A have been arranged or otherwise placed within the phantom body structure 202.

Generally speaking, the optical signal modulator may send one or more light pulses through individual fibers in a systematic manner. The sensor(s) detect the resultant signals generated by the photoreceiver, and this information is fed back to the controller to create a 3D map of the photoreceiver locations.

In one particular example, controller 602 (e.g., controller 252 of FIG. 2B) can actuate the light source(s) 604 (e.g., light source(s) 260) as shown by the dashed line and/or the optical signal modulator 606 (e.g., signal modulator 258) as shown by the solid line to generate one or more test signals that are propagated along selected ones of the optical fibers. By way of example, in an initial setup procedure this may be done one fiber at a time. For each modulated light signal propagated along a selected fiber, the corresponding optode generates an electrical output signal. As shown, depending on the modulated optical signal(s), the optodes may output different electrical signals 608*a*, 608*b*, . . . , 608*n*. The modulated optical signals may be chosen so that the output electrical signals 608 are readily detectable, for instance to have an amplitude that exceeds a particular threshold (e.g., 1.0*v* or more or less).

Similar to what was described above with regard to FIG. 2A, the sensors 208 can be used to detect the electrical signal(s) 608 generated by each optode. Here, the sensors 208 provide the electrical signal information to detection system 610 (e.g., receiver device 210). Raw or processed signal information is fed back to controller 602. The controller 602 uses this signal information to generate a 3D map of the location of each optode within the phantom body. In one scenario, the location of each sensor around the phantom body is known to the controller. Thus, when different sensors detect an electrical signal from a given optode, the controller may process the received signal information via, e.g., triangulation or trilateration to pinpoint the specific location of the given optode. In accordance with one aspect of the technology, machine learning or other techniques can aid in the mapping process.

In addition to mapping the exact or relative location for each optode within the phantom, feedback to the controller 602 can be used for calibration and diagnostic purposes. By way of example, for each biopotential simulation the system can be evaluated to ensure proper actuation of the optodes. This allows the system to compensate for channel-by-channel variability due to manufacturing tolerances, aging, phantom substrate electrochemical shifts, and environmental conditions, as well as to identify defective fibers, optode, sensors, detectors, or modulation paths. Factors that can impact the signals received by each external sensor include the distance from the optodes, the properties of the bulk substrate, the overall efficiency of the optical to electrical conversion at each optode tip, the amplitude and waveform of the optode driving light source, and the relative timing and superposition of signals from surrounding optodes. Thus, a calibration process to normalize or level such signals may be performed after or in conjunction with the mapping process.

One significant advantage to this system is the reproducibility of signals for different biopotential scenarios. Each scenario can be reproduced with a very high degree of fidelity using digital-based optical signaling, so that the same pattern can be tested and analyzed over time. And since the system uses optical signaling, issues such as electrical crosstalk are avoided, which allows for very sensitive testing techniques such as MEG testing.

Another important advantage is the ability to easily configure the bio-phantom and detect or otherwise determine the exact placement of the optodes that will generate the electrical signals for the biopotential scenarios. Defects or failures can the tested and the system can adapt accordingly. For instance, should one or more optodes fail, or light not propagate along a given fiber in the desired manner, the controller may adjust the modulation technique and/or light sources to achieve the particular biopotential scenario to be evaluated.

As noted above, the sensors positioned at the surface of the phantom body structure are configured to detect electrical signals generated by one or more of the optically excited optodes within the phantom. The detected electrical signals output by the optodes can be a complex blend from different optode sources, such as can occur in an actual biological equivalent. By using optical fibers and other non-metallic components, the phantom need not include any magnetic materials. This will avoid interference with extremely sensitive sensors, such as MEG sensors. It also enables the reproducibility of signals, which can be particularly beneficial for receiver calibration and machine learning.

Figure 7:
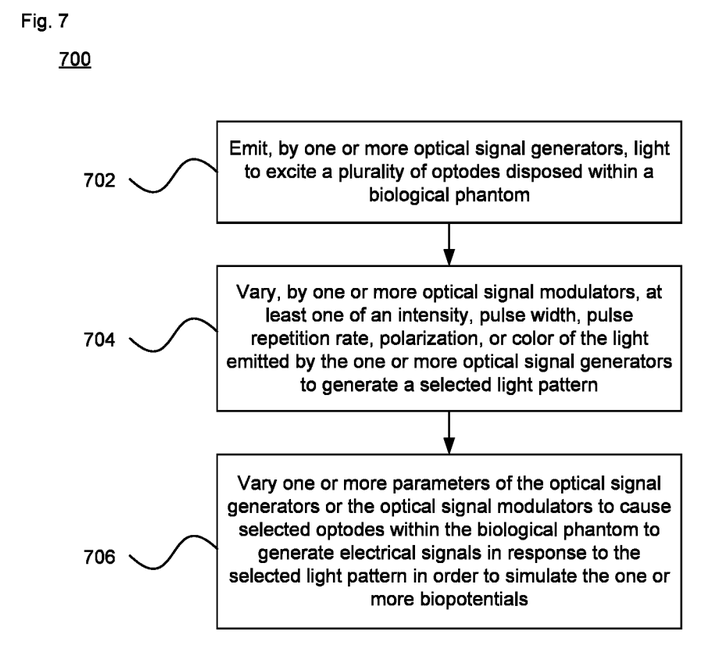
FIG. 7 illustrates an example method in accordance with aspects of the technology.

FIG. 7. illustrates an example 700 of a method of simulating one or more biopotentials for a biological phantom. As shown in block 702, the method includes emitting, by one or more optical signal generators, light to excite a plurality of optodes disposed within the biological phantom. At block 704, one or more optical signal modulators varies at least one of an intensity, pulse width, pulse repetition rate, polarization, or color of the light emitted by the one or more optical signal generators to generate a selected light pattern. And at block 706, one or more parameters of the optical signal generators or the optical signal modulators are varied to cause selected ones of the plurality of optodes within the biological phantom to generate electrical signals in response to the selected light pattern in order to simulate the one or more biopotentials.

The one or more biopotentials may correspond to one or more types of brain activity. For instance, the brain activity may be one or more of Alpha waves, Beta waves, Delta waves, Theta waves, sleep spindles, slow-waves and seizure activity.

The method may further include repeating the varying of the one or more parameters. This causes the plurality of optodes to reproduce the generated electrical signals one or more times. The method may include multiplexing the selected light pattern across a set of optical fibers, wherein each of the optical fibers in the set is coupled to a corresponding one of the plurality of optodes. The method may also include calibrating an optical modulation and control module (e.g., module 212 of FIG. 2B) in response to the simulated one or more biopotentials. And varying the one or more parameters of the optical signal generators or the optical signal modulators may be performed based on a 2D or 3D arrangement of the plurality of optodes within the biological phantom.

Figure 8:
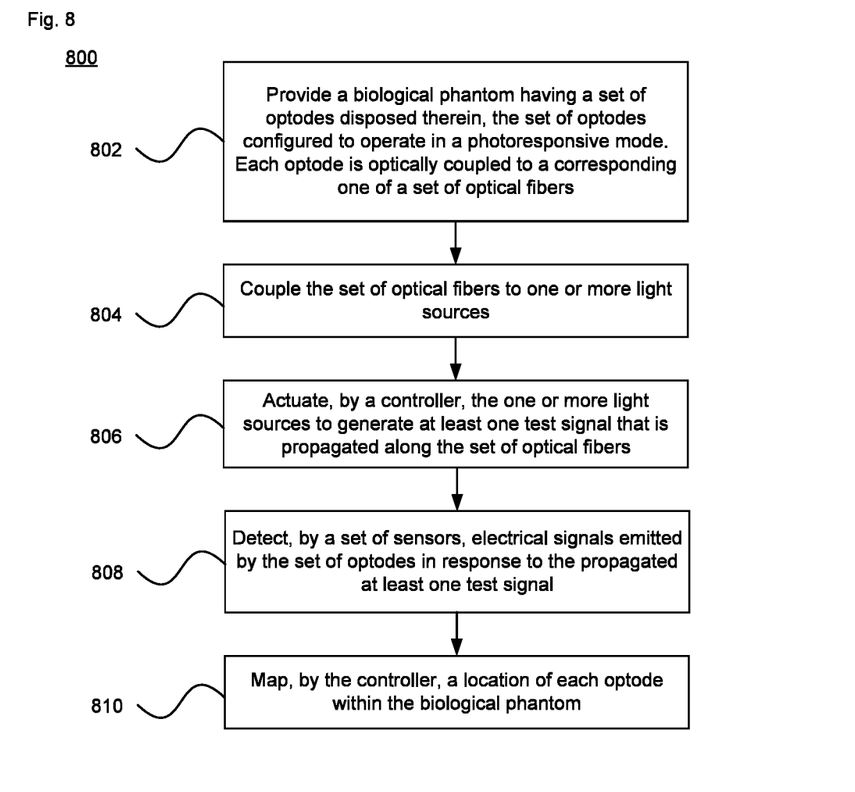
FIG. 8 illustrates another example method in accordance with aspects of the technology.

FIG. 8. illustrates an example 800 of a method that includes providing, at block 802, a biological phantom having a set of optodes disposed therein. The set of optodes is configured to operate in a photoresponsive mode. Each one of the set of optodes is optically coupled to a corresponding one of a set of optical fibers. At block 804, the set of optical fibers is coupled to one or more light sources. At block 806, a controller actuates the one or more light sources to generate at least one test signal that is propagated along the set of optical fibers. At block 808, a set of sensors detects electrical signals emitted by the set of optodes in response to the propagated at least one test signal. And at block 810, the control maps a location of each optode within the biological phantom. The at least one test signal can include distinct signals applied to one or more of the optical fibers, which allows for tightly controlled testing and calibration of the system.

Actuating the one or more light sources to generate the at least one test signal can be performed to propagate the at least one test signal along one fiber at a time and/or performed using time division multiplexing. Alternatively or additionally, actuating the one or more light sources to generate the at least one test signal may include the controller actuating an array of light shutters to produce time varying pixels associated with individual fibers of the set of optical fibers. In one scenario, actuating the one or more light sources to generate the at least one test signal includes varying one or more of an intensity, pulse width, pulse duration, polarization or color of the at least one test signal. Actuating the one or more light sources to generate the at least one test signal may alternatively or additionally include modulating optical signals so that the electrical signals emitted by the set of optodes have amplitudes that exceed a threshold value.

Mapping the location of each optode within the biological phantom can include evaluating the detected electrical signals based on known locations of the set of sensors. And evaluating the detected electrical signals based on known locations of the set of sensors may comprise performing triangulation or trilateration to identify a specific location of a given optode of the set of optodes within the biological phantom.

The method may further comprise performing a calibration operation based on the mapping of the location of each optode within the biological phantom. The calibration operation may include identifying one or more of a defective optical fiber, a defective optode, or a defective sensor. The calibration operation may alternatively or additionally include performing a normalization process to account for variations in signal level of the electrical signals emitted by the set of optodes.

The method may also include detecting either (i) failure of a given optode in the set of optodes or (ii) failure to propagate the at least one test signal along a given fiber of the set of optical fibers. In response to detecting (i) or (ii), the controller adjusts either a modulation technique or the one or more light sources. Furthermore, adjusting either the modulation technique or the one or more light sources may include modifying the at least one test signal propagated along the set of optical fibers to produce a selected pattern by the optodes that have not failed.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements. The processes or other operations may be performed in a different order or simultaneously, unless expressly indicated otherwise herein.

The invention claimed is:

1. A biopotential control system for use with a biological phantom to simulate one or more biopotentials, the system comprising:
    an optical control module including:
        one or more optical signal generators configured to emit light to excite a plurality of optodes disposed within the biological phantom, the one or more optical signal generators being coupled to a plurality of optical fibers each having a portion thereof received within a body structure of the biological phantom, each optical fiber being operatively coupled to a corresponding one of the plurality of optodes;
        one or more optical signal modulators coupled to the one or more optical signal generators, the one or more optical signal modulators being configured to vary at least one of an intensity, pulse width, pulse repetition rate, polarization, or color of the light emitted by the one or more optical signal generators; and
        a controller coupled to one or both of the optical signal generators and the optical signal modulators, the controller being configured to vary one or more parameters of the optical signal generators or the optical signal modulators to cause selected ones of the plurality of optodes within the biological phantom to generate electrical signals in order to simulate the one or more biopotentials.

2. The biopotential control system of claim 1, further comprising a receiver module including a set of sensors configured to detect electrical signals generated by the plurality of optodes in response to a simulated biopotential.

3. The biopotential control system of claim 2, wherein the set of sensors of the receiver module are selected from the group consisting of electroencephalograph (EEG), electrocardiogram (ECG), electromyogram (EMG) or magnetoencephalography (MEG) sensors.

4. The biopotential control system of claim 2, wherein the controller is configured to receive feedback from the receiver module to map physical locations of the optodes within the body structure of the biological phantom.

5. The biopotential control system of claim 1, wherein the one or more optical signal generators are lasers or light emitting diodes (LEDs).

6. The biopotential control system of claim 5, wherein the one or more optical signal generators are arranged as a one-, two-, or three-dimensional LED matrix.

7. The biopotential control system of claim 1, wherein the one or more optical signal generators comprise a plurality of optical signal generators, each of the plurality of optical signal generators being optically coupled to a given one of the plurality of optical fibers.

8. The biopotential control system of claim 1, wherein the one or more optical signal modulators comprise a one or two-dimensional array of light shutters.

9. The biopotential control system of claim 1, further comprising the plurality of optical fibers.

10. The biopotential control system of claim 1, further comprising the biological phantom and the plurality of optodes.

11. The biopotential control system of claim 1, wherein the controller is further configured to calibrate the biopotential control system to account for channel-by-channel variability due to at least one of manufacturing tolerances, aging, electrochemical shifts in the body structure of the biological phantom, or environmental conditions.

12. The biopotential control system of claim 1, wherein the controller is further configured to identify a defect in one of the plurality of optical fiber, one of the plurality of optodes, a modulation path, a sensor or a receiver module.

13. A method of simulating one or more biopotentials for a biological phantom, the method comprising:
    emitting, by one or more optical signal generators, light to excite a plurality of optodes disposed within the biological phantom;
    varying, by one or more optical signal modulators, at least one of an intensity, pulse width, pulse repetition rate, polarization, or color of the light emitted by the one or more optical signal generators to generate a selected light pattern; and
    varying one or more parameters of the optical signal generators or the optical signal modulators to cause selected ones of the plurality of optodes within the biological phantom to generate electrical signals in response to the selected light pattern in order to simulate the one or more biopotentials.

14. The method of claim 13, further comprising repeating the varying of the one or more parameters to cause the plurality of optodes to reproduce the generated electrical signals one or more times.

15. The method of claim 13, further comprising multiplexing the selected light pattern across a set of optical fibers, each of the optical fibers in the set being coupled to a corresponding one of the plurality of optodes.

16. The method of claim 13, further comprising calibrating an optical modulation and control module in response to the simulated one or more biopotentials.

17. A method comprising:
- providing a biological phantom having a set of optodes disposed therein, the set of optodes configured to operate in a photoresponsive mode, each one of the set of optodes being optically coupled to a corresponding one of a set of optical fibers;
- coupling the set of optical fibers to one or more light sources;
- actuating, by a controller, the one or more light sources to generate at least one test signal that is propagated along the set of optical fibers;
- detecting, by a set of sensors, electrical signals emitted by the set of optodes in response to the propagated at least one test signal; and
- mapping, by the controller, a location of each optode within the biological phantom.

18. The method of claim 17, wherein actuating the one or more light sources to generate the at least one test signal includes varying one or more of an intensity, pulse width, pulse duration, polarization or color of the at least one test signal.

19. The method of claim 17, further comprising performing a calibration operation based on the mapping of the location of each optode within the biological phantom.

20. The method of claim 17, further comprising:
- detecting either (i) failure of a given optode in the set of optodes or (ii) failure to propagate the at least one test signal along a given fiber of the set of optical fibers;
- in response to the detecting, the controller adjusting either a modulation technique or the one or more light sources.

* * * * *